United States Patent
Bradford et al.

(10) Patent No.: US 8,013,002 B2
(45) Date of Patent: *Sep. 6, 2011

(54) METHODS OF ADMINISTERING PIRFENIDONE THERAPY

(75) Inventors: Williamson Ziegler Bradford, Ross, CA (US); Javier Szwarcberg, San Francisco, CA (US)

(73) Assignee: Intermune, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/049,894

(22) Filed: Mar. 16, 2011

(65) Prior Publication Data

US 2011/0166186 A1 Jul. 7, 2011

Related U.S. Application Data

(63) Continuation of application No. 12/901,245, filed on Oct. 8, 2010, now Pat. No. 7,910,610, which is a continuation of application No. 12/684,879, filed on Jan. 8, 2010, now Pat. No. 7,816,383.

(60) Provisional application No. 61/266,815, filed on Dec. 4, 2009.

(51) Int. Cl.
| | |
|---|---|
| A01N 43/40 | (2006.01) |
| A01N 33/24 | (2006.01) |
| A01N 33/02 | (2006.01) |
| A61K 31/44 | (2006.01) |
| A61K 31/15 | (2006.01) |
| A61K 31/135 | (2006.01) |

(52) U.S. Cl. ......... 514/350; 514/354; 514/640; 514/646
(58) Field of Classification Search .................. 514/350, 514/354, 640, 646
See application file for complete search history.

(56) References Cited

U.S. PATENT DOCUMENTS

| | | | |
|---|---|---|---|
| 5,310,562 A | 5/1994 | Margolin | |
| 5,518,729 A | 5/1996 | Margolin | |
| 5,716,632 A | 2/1998 | Margolin | |
| 7,407,973 B2 | 8/2008 | Ozes et al. | |
| 7,566,729 B1 | 7/2009 | Bradford et al. | |
| 7,605,173 B2 | 10/2009 | Seth | |
| 7,635,707 B1 | 12/2009 | Bradford et al. | |
| 7,696,236 B2 | 4/2010 | Bradford | |
| 7,728,013 B2 | 6/2010 | Blatt et al. | |
| 2006/0110358 A1 | 5/2006 | Hsu | |
| 2007/0053877 A1 | 3/2007 | Crager et al. | |
| 2007/0054842 A1 | 3/2007 | Blatt et al. | |
| 2007/0072181 A1 | 3/2007 | Blatt | |
| 2007/0092488 A1 | 4/2007 | Strieter et al. | |
| 2007/0117841 A1 | 5/2007 | Ozes et al. | |
| 2007/0172446 A1 | 7/2007 | Blatt | |
| 2007/0203202 A1 | 8/2007 | Robinson et al. | |
| 2007/0203203 A1 | 8/2007 | Tao et al. | |
| 2008/0003635 A1 | 1/2008 | Ozes et al. | |
| 2008/0019942 A1 | 1/2008 | Seiwert et al. | |
| 2008/0194644 A1 | 8/2008 | Bradford | |
| 2008/0287508 A1 | 11/2008 | Robinson et al. | |
| 2009/0170804 A1 | 7/2009 | Phillips et al. | |
| 2009/0191265 A1 | 7/2009 | Radhakrishnan et al. | |
| 2009/0197923 A1 | 8/2009 | Bradford | |
| 2009/0318455 A1 | 12/2009 | Kossen et al. | |
| 2010/0152250 A1 | 6/2010 | Radhakrishnan et al. | |

FOREIGN PATENT DOCUMENTS

EP 1138329 A2 10/2001

OTHER PUBLICATIONS

Aloxie® (palonosetron) package insert, Rev. Feb. 2008 ("Palonosetron package insert").
Azuma et al., Double-blind, placebo-controlled trial of pirfenidone in patients with idiopathic pulmonary fibrosis. *Am. J. Respir. Crit. Care Med.* 171: 1040-7 (2005).
BuSpar® (buspirone HCI, USP) package insert (Mar. 2007).
Clozaril® (clozapine) package insert (Jan. 2010).
Correspondence received from FDA (2010).
Dolophine Hydrochloride (methadone hydrochloride) package insert (Sep. 2009).
European search report from EP 10250379.4 dated May 17, 2010.
FDA Briefing Information for the Mar. 9, 2010 Meeting of the Pulmonary-Allergy Drugs Advisory Committee (Contains the Clinical Briefing Document (Banu Karimi-Shah, M.D., Clinical Reviewer, Division of Pulmonary and Allergy Products, NDA 22-535) beginning on p. 21), published at <http://www.fda.gov/downloads/AdvisoryCommittees/CommitteesMeetingMaterials/Drugs/Pulmonary-AllergyDrugsAdvisoryCommittee/UCM203081.pdf>.
Food and Drug Administration Center for Drug Evaluation and Research, Pulmonary-Allergy Drugs Advisory Committee (PADAC) Meeting Transcript (Tuesday, Mar. 9, 2010), published at <http://www.fda.gov/downloads/AdvisoryCommittees/CommitteesMeetingMaterials/Drugs/Pulmonary-AllergyDrugsAdvisoryCommittee/UCM208806.pdf>.
Hemeryck et al. 2002, Selective serotonin reuptake inhibitors and cytochrome P-450 mediated drug-drug interactions: An update, Current Drug Metabolism, vol. 3, pp. 13-37.
Inderal® (propranolol hydrochloride capsule, extended release) package insert (Nov. 2007).
Inderal® (propranolol hydrochloride, long-acting capsules) package insert (Nov. 2007).
Jeppesen et al., "Dose-dependent inhibition of CYP1A2, CYP2C19 and CYP2D6 by citalopram, fluoxetine, fluovaxamine and paroxetine," European Journal of Clinical Pharmacology, 41(1):73-78 (1996).
Landi, et al., "Human cytochrome P4501A2." IARC Scientific Publications 148:173-195 (1999).
Lexotan (bromazepam) package insert (Feb. 2007).
Malarone® (atovaquone and proguanil hydrochloride) package insert (2008).
Mexitil® (mexiletine hydrochloride, USP) package insert (2003).
Naropin® (ropivacaine hydrochloride monohydrate) package insert (Nov. 2008).
Odansetron product information from the UK Medicines and Healthcare Products Regulatory Agency ("Odansetron UK product information") (Mar. 14, 2007).

(Continued)

*Primary Examiner* — Sreeni Padmanabhan
*Assistant Examiner* — Kara R McMillian
(74) *Attorney, Agent, or Firm* — Marshall, Gerstein & Borun LLP; John A. Bendrick

(57) ABSTRACT

The present invention relates to methods involving avoiding adverse drug interactions with fluvoxamine and pirfenidone or other moderate to strong inhibitors of CYP enzymes.

11 Claims, 1 Drawing Sheet

OTHER PUBLICATIONS

Pirfenidone NDA 22-535 Pulmonary-Allergy Drugs Advisory Committee Mar. 9, 2010, slide deck (InterMune, Inc.), published at <http://wwvv.fda.gov/downloads/AdvisoryCommittees/CommitteesMeetingMaterials/Drugs/Pulmonary-AllergyDrugsAdvisoyCommittee/UCM206399.pdf>.

Pulmonary-Allergy Drugs Advisory Committee Meeting, Pirfenidone Capsules, NDA 22-535, S-000, Mar. 9, 2010, slide deck (U.S. Food and Drug Administration), published at <http://www.fda.gov/downloads/AdvisoryCommittees/CommitteesMeetingMaterials/Drugs/Pulmonary-AllergyDrugsAdvisoryCommittee/UCM206398.pdf>.

Quinidine Gluconate package insert (2002).

Remington's: the Science and Practice of Pharmacy, Nineteenth Edition, vol. 1, p. 806 (1985).

Thioridazine Hydrochloride package insert (May 2009).

Tofranil (imipramine hydrochloride) package insert (Aug. 2007).

Zofran® (odansetron) package insert ("Odansetron package insert"), Apr. 2002.

Zyprexa® (olanzapine) package insert, Rev. Jan. 27, 2010 ("Olanzapine package insert").

Taniguchi, et al., "Pirfenidone in idiopathic pulmonary fibrosis," Eur Respir J, and online supplement, 35:821-829 (2010).

Shionogi & Co., Ltd., Pirespa Tablet Packaging Label, Prepared Oct. 2008.

Shionogi & Co., Ltd., Pirespa Tablet Report on the Deliberation Results, Evaluation and Licensing Division, Pharmaceutical and Food Safety Bureau, Ministry of Health, Labour and Welfare (Sep. 16, 2008).

InterMune, Pirfendione Briefing Document (Publication date Mar. 9, 2010).

International Search Report and Written Opinion of related case PCT/US10/058943, (Feb. 1, 2011).

Antoniu, Pirfenidone for the treatment of idiopathic pulmonary fibrosis. Expert Opinion on Investigational Drugs 15: 823-828 (2006).

Scriabine et al., New developments in the therapy of pulmonary fibrosis. Advances in Pharmacology 57: 419-464 (2009).

METHODS OF ADMINISTERING PIRFENIDONE THERAPY

CROSS REFERENCE TO RELATED APPLICATIONS

This application is a continuation of U.S. patent application Ser. No. 12/901,245, filed Oct. 8, 2010, now U.S. Pat. No. 7,910,610, which is a continuation of U.S. patent application Ser. No. 12/684,879, filed Jan. 8, 2010, now U.S. Pat. No. 7,816,383, which claims the priority benefit under 35 U.S.C. §119(e) of U.S. Provisional Application No. 61/266,815, filed Dec. 4, 2009, each of which is incorporated herein by reference in their entirety.

FIELD OF THE INVENTION

The invention relates to improved methods of administering pirfenidone therapy involving avoiding adverse drug interactions with fluvoxamine, a strong inhibitor of CYP1A2.

BACKGROUND

Pirfenidone is small molecule with a molecular weight of 185.23 daltons whose chemical name is 5-methyl-1-phenyl-2-(1H)-pyridone. Pirfenidone has anti-fibrotic properties and has been investigated for therapeutic benefits to patients suffering from various fibrotic conditions. It is approved in Japan for treatment of idiopathic pulmonary fibrosis (IPF) under the trade name Pirespa®.

Pirfenidone has been shown to be metabolized by various isoforms of the cytochrome P450 (CYP) protein [See the Report on the Deliberation Results, Evaluation and Licensing Division, Pharmaceutical and Food Safety Bureau, Ministry of Health Labour and Welfare, Sep. 16, 2008]. Specifically, several cytochrome P450 (CYP) isoforms (CYP1A2, 2C9, 2C19, 2D6 and 2E1) were involved in the earliest stages of oxidative metabolism of pirfenidone.

Fluvoxamine belongs to a class of therapeutics known as selective serotonin reuptake inhibitors (SSRIs). The SSRIs are a group of antidepressants with similar pharmacologic effects, but with different chemical structures. Fluvoxamine has been approved for treatment of social anxiety disorder (social phobia), obsessive compulsive disorder (OCD), and has been prescribed to treat major depression, and other anxiety disorders such as panic disorder and post-traumatic stress disorder [McClellan et al., (Drugs October 2000). "Fluvoxamine An Updated Review of its Use in the Management of Adults with Anxiety Disorders". *Adis Drug Evaluation* 60 (4): 925-954]. In addition to fluvoxamine, other clinically available SSRIs are citalopram, fluoxetine, paroxetine and sertraline. The elimination of these lipophilic compounds proceeds predominantly via oxidation catalysed by CYP in the liver. SSRIs have the potential for inhibition of CYP enzymes [Brosen, The pharmacogenetics of the selective serotonin reuptake inhibitors. *Clin Invest* 71(12):1002-1009, 1993]. Jeppesen et al. reported that fluvoxamine is a potent inhibitor of CYP1A2 in humans in vivo [Jeppesen et al., Dose-dependent inhibition of CYP1A2, CYP2C19 and CYP2D6 by citalopram, fluoxetine, fluvoxamine and paroxetine. *Eur J Clin Pharmacol* 51: 73-78, 1996]. Fluvoxamine has also been shown to be a very potent inhibitor of CYP1A2 in vitro [Brosen et al., Fluvoxamine is a potent inhibitor of cytochrome P4501A2. *Biochem Pharmacol* 45:1211-1214, 1993; Rasmussen et al., Selective serotonin reuptake inhibitors and theophylline metabolism in human liver microsomes: potent inhibition by fluvoxamine. *Br J Clin Pharmacol* 39:151-159, 1995].

SUMMARY OF THE INVENTION

The invention disclosed herein is based on the discovery of an adverse drug interaction between pirfenidone and fluvoxamine.

The invention generally relates to improved methods of administering pirfenidone to a patient in need of pirfenidone therapy, and to methods of preparing or packaging pirfenidone medicaments, containers, packages and kits. In any of the aspects or embodiments, the patient may have idiopathic pulmonary fibrosis (IPF) and the medicament is for treatment of IPF. In any of the aspects or embodiments, the therapeutically effective amount of pirfenidone being administered may be a daily dosage of 2400 mg or 2403 mg per day. In any of the aspects of the invention, the daily dosage may be administered in divided doses three times a day, or two times a day, or alternatively is administered in a single dose once a day. In any of the aspects of the invention, the pirfenidone may be administered with food. For example, the daily dosage of 2400 mg or 2403 mg pirfenidone per day may be administered as follows: 801 mg taken three times a day, with food.

In some aspects, the invention provides a method of administering pirfenidone therapy to a patient in need of pirfenidone therapy (e.g., a patient with IPF), involving administering to the patient a therapeutically effective amount of pirfenidone, and avoiding administration of fluvoxamine.

In other aspects, the invention provides a method of administering pirfenidone therapy to a patient in need of pirfenidone therapy, comprising discontinuing administration of fluvoxamine to avoid an adverse drug interaction and administering a therapeutically effective amount of pirfenidone. In one embodiment, the patient is receiving fluvoxamine, and fluvoxamine is discontinued concurrent with starting administration of pirfenidone. In another embodiment, fluvoxamine is discontinued within at least 3 days to 1 month prior to or after starting pirfenidone therapy. This time period, for example, permits adequate time for tapering and withdrawal without adverse effects. In one example, in a method of administering a therapeutically effective amount of pirfenidone to a patient with IPF, the invention provides an improvement that comprises avoiding or discontinuing administration of fluvoxamine and administering a therapeutically effective amount of pirfenidone.

In yet other aspects, a method of administering pirfenidone therapy to a patient in need of pirfenidone therapy and in need of fluvoxamine therapy is provided, comprising administering a therapeutically effective amount of pirfenidone to the patient, and administering an alternative therapy that is not fluvoxamine. In one aspect, the alternative therapy that is not fluvoxamine is a drug that is not a moderate to strong inhibitor of CYP1A2. Preferably, such drug is not a moderate to strong inhibitor of both CYP1A2, and another CYP enzyme selected from the group consisting of CYP3A4, CYP2C9, and/or CYP2C19. In some examples, the alternative drug is selected from the group consisting of Citalopram (Celexa), Escitalopram (Lexapro), Fluoxetine (Prozac, Prozac Weekly), Paroxetine (Paxil, Paxil CR, Pexeva), and/or Sertraline (Zoloft).

In some aspects, the invention provides a method of administering pirfenidone therapy to a patient in need of pirfenidone therapy (e.g., a patient with IPF), involving administering to the patient a therapeutically effective amount of pirfenidone, and advising the patient in any one, two, three or more of the following ways:

(a) advising the patient that fluvoxamine should be avoided or discontinued, (b) advising the patient that co-administration of pirfenidone with drugs that are moderate to strong inhibitors of both CYP1A2 and another CYP enzyme selected from the group consisting of CYP3A4, CYP2C9, and/or CYP2C19., can alter the therapeutic effect or adverse reaction profile of pirfenidone, (c) advising the patient that co-administration of pirfenidone with fluvoxamine can alter the therapeutic effect or adverse reaction profile of pirfenidone, (d) advising the patient that use of pirfenidone in patients being treated with fluvoxamine is contraindicated, (e) advising the patient that co-administration of pirfenidone and fluvoxamine resulted in an average 6-fold increase in exposure to pirfenidone, and/or.

(f) advising the patient that strong CYP1A2 inhibitors should be used with caution in patients receiving pirfenidone due to the potential for reduced pirfenidone clearance.

In some embodiments, the method further includes advising the patient that co-administration of pirfenidone and fluvoxamine resulted in a 2-fold increase in average peak serum concentration of pirfenidone (Cmax). In yet further embodiments, the method also includes avoiding administering a strong CYP1A2 inhibitor, or discontinuing administration of a strong CYP1A2 inhibitor.

In some embodiments, a method of reducing toxicity of pirfenidone treatment in a patient is provided comprising administering a therapeutically effective amount of pirfenidone to the patient and advising the patient of any of the foregoing advice.

In some embodiments, a method of improving safety of pirfenidone treatment in a patient is provided comprising administering a therapeutically effective amount of pirfenidone to the patient and advising the patient of any of the foregoing advice.

In some embodiments, a method of reducing adverse drug interaction with pirfenidone treatment in a patient is provided comprising administering a therapeutically effective amount of pirfenidone to the patient and advising the patient of any of the foregoing advice.

DETAILED DESCRIPTION OF THE INVENTION

Figure 1:
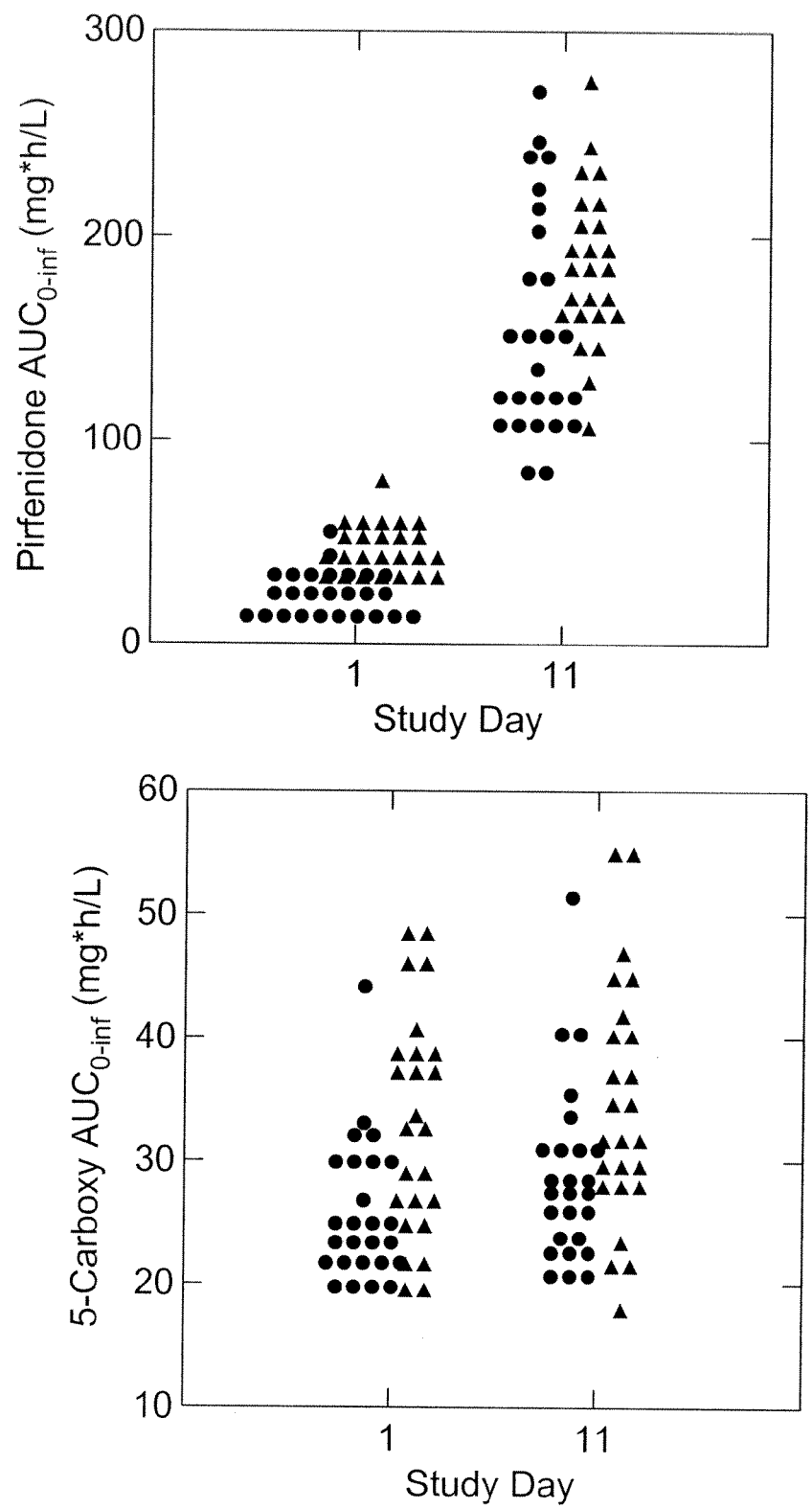
FIG. 1 depicts a symmetrical dot plot of $AUC_{0-\infty}$ estimates by study day—circles indicate smokers, triangles indicate nonsmokers.

Pirfenidone is an orally active, anti-fibrotic agent. Results of in vitro experiments indicated that pirfenidone is primarily metabolized by CYP1A2 (approx. 48%) with multiple other CYPs contributing as well (each <13%) (i.e., 1A1, 2A6, 2B6, 2C8, 2C9, 2C18, 2C19, 2D6, 2E1, 2J2, 3A4, 3A5, 4A11, and 4F2). Oral administration of pirfenidone results in the formation of four metabolites, 5 hydroxymethyl-pirfenidone, 5 carboxy-pirfenidone, 4'-hydroxy-pirfenidone, and the 5 O-acyl glucuronide metabolite of 5 carboxy-pirfenidone. In humans, only pirfenidone and 5-carboxy-pirfenidone are present in plasma in significant quantities; none of the other metabolites occur in sufficient quantities to allow for PK analysis. There are no unique human metabolites.

Fluvoxamine is a potent CYP1A2 and CYP2C19 inhibitor, and a moderate CYP2C9, CYP2D6, and CYP3A4 inhibitor [Hemeryck et al., Selective Serotonin Reuptake Inhibitors and Cytochrome P-450 Mediated Drug-Drug Interactions: An Update. *Current Drug Metabolism* 3(1): 13-37, 2002].

The invention disclosed herein is based on the discovery of an adverse drug interaction between pirfenidone and fluvoxamine. Adverse drug interactions represent 3-5% of preventable in-hospital adverse drug reactions, and are an important contributor to the number of emergency room visits and hospital admissions [Leape L L et al., JAMA 1995;274(1):35-43; Raschetti R et al. Eur J Clin Pharmacol 1999;54(12):959-963].

Data reported herein show that co-administration of pirfenidone with fluvoxamine resulted in an average 6-fold increase in exposure (AUC, or area under the curve) to pirfenidone. It also resulted in an average 2-fold increase in Cmax, the mean maximum plasma concentration. Depending on the circumstances, FDA draft guidance suggests that a drug-drug interaction is present when comparisons indicate twofold or greater systemic exposure for a drug when given in combination with the second drug, compared to when given alone. FDA Preliminary Concept Paper, "Drug Interaction Studies—Study Design, Data Analysis, and Implications for Dosing and Labeling," Oct. 1, 2004.

Definitions

The terms "therapeutically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, or reduction in symptoms. The precise effective amount for a subject will depend upon the subject's body weight, size, and health; the nature and extent of the condition; and the therapeutic or combination of therapeutics selected for administration. Where a drug has been approved by the U.S. Food and Drug Administration (FDA), a "therapeutically effective amount" refers to the dosage approved by the FDA or its counterpart foreign agency for treatment of the identified disease or condition.

As used herein, a patient "in need of pirfenidone therapy" is a patient who would benefit from administration of pirfenidone. The patient may be suffering from any disease or condition for which pirfenidone therapy may be useful in ameliorating symptoms. Such diseases or conditions include pulmonary fibrosis, idiopathic pulmonary fibrosis, idiopathic interstitial pneumonia, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, and/or skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute and chronic renal disease; renal fibrosis, irritable bowel syndrome; pyresis; restenosis; cerebral malaria; stroke and ischemic injury; neural trauma; Alzheimer's disease; Huntington's disease; Parkinson's disease; acute and chronic pain; allergies, including allergic rhinitis and allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and auto-immune diseases, such as multiple sclerosis, lupus and fibromyalgia; AIDS and other viral diseases such as Herpes Zoster, Herpes Simplex I or II, influenza virus, Severe Acute Respiratory Syndrome (SARS) and cytomegalovirus; and diabetes mellitus. In addition, the methods of the embodiments can be used to treat proliferative disorders (including both benign and malignant hyperplasias), including acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases, and the like; pain disorders including neuromuscular pain, headache, cancer pain, dental pain, and arthritis pain; angiogenic disorders including solid tumor angiogenesis, ocular neovascularization, and infantile hemangioma; conditions associated with the cyclooxygenase and lipoxygenase signaling pathways, including conditions associated with prostaglandin endoperoxide synthase-2 (including edema, fever, analgesia, and pain); organ hypoxia; thrombin-induced platelet aggregation; protozoal diseases.

As used herein, a patient in need of "fluvoxamine therapy" is understood to be a patient in need of "selective serotonin reuptake inhibitor (SSRI) therapy." Such patients include patients suffering from social anxiety disorder (social phobia), obsessive compulsive disorder (OCD), depression, anxiety disorders, panic disorder and post-traumatic stress disorder.

For CYP enzymes, the FDA generally defines a "strong inhibitor" as one that caused a >5-fold increase in the plasma AUC values or more than 80% decrease in clearance of CYP substrates (not limited to sensitive CYP substrate) in clinical evaluations. The FDA generally defines a "moderate inhibitor" as one that caused a >2- but <5-fold increase in the AUC values or 50-80% decrease in clearance of sensitive CYP substrates when the inhibitor was given at the highest approved dose and the shortest dosing interval in clinical evaluations.

CYP Inhibitors and Substrates

In any of the embodiments described herein, including but not limited to the treatment methods involving the advice, warnings, discontinuation or dose titration downwards, the packages and kits, and/or the methods of preparing or packaging pirfenidone, the methods, packages, kits, advice, warnings, discontinuation or dose titration may apply not only to fluvoxamine but also to any other drug that is a moderate to strong inhibitor of both CYP1A2 and another CYP enzyme selected from the group consisting of CYP3A4, CYP2C9, and/or CYP2C19, such as fluvoxamine. The embodiments may also apply to any other drug that is a moderate to strong inhibitor of both CYP1A2 and another CYP enzyme selected from the group consisting of CYP3A4, CYP2C9, CYP2C19, CYP2B6, and/or CYP2D6. The embodiments may also apply to any other drug that is a moderate to strong inhibitor of both CYP1A2 and another CYP enzyme that metabolizes pirfenidone, e.g. selected from the group consisting of CYP1A1, CYP2A6, CYP2B6, CYP2C8, CYP2C9, CYP2C18, CYP2C19, CYP2D6, CYP2E1, CYP2J2 CYP3A4, CYP3A5, CYP4A11 and/or CYP4F2.

As yet other alternatives, in any of the embodiments described herein, including but not limited to the treatment methods involving the advice, warnings, discontinuation or dose titration downwards, the packages and kits, and/or the methods of preparing or packaging pirfenidone, the methods, packages, kits, advice, warnings, discontinuation or dose titration may apply not only to fluvoxamine but also to any other drug that is a strong inhibitor of CYP1A2 or a substrate for CYP1A2.

CYP1A2 metabolizes many commonly used drugs including theophylline, imipramine, propranolol, and clozapine. These drugs are commonly referred to as "substrates" for CYP1A2. Additional CYP1A2 substrates include but are not limited to acetominophen, amitriptyline, caffeine, chlordiazepoxide, cinacalcet, clomipramine, clopidogrel, cyclobenzaprine, desipramine, diazepam, duloxetine, erlotinib, estradiol, flutamide, haloperidol, levobupivacaine, methadone, mirtazapine, naproxen, nortriptyline, olanzapine, ondansetron, ramelteon, riluzole, ropinirole, ropivacaine, tacrine, tizanidine, verapamil, and warfarin.

Inhibitors of CYP1A2 include fluvoxamine, cimetidine, amiodarone, echinacea, enoxacin, norfloxacin, oral contraceptives, tacrine, ticlopidine, and many fluoroquinolone antibiotics. Moderate inhibitors of CYP1A2 include ciprofloxacin, mexiletine, propafenone and zileuton. Additional inhibitors of CYP1A2 include atazanavir, citalopram, clarithromycin, dilitiazem, erythromycin, ethinyl estradiol, isoniazid, ketoconazole, methoxsalen, nalidixic acid, norethindrone, omeprazole, paroxetine, tipranvir, and troleandomycin. Other inhibitors of CYP1A2 include acyclovir, caffeine, famotidine, flutamide, grapefruit juice, lidocaine, lomefloxacin, moclobemide, ofloxacin, perphenazine, phenacetin, propafenone, ropinirole, tocainide, and verapamil.

Inhibitors of CYP3A4 include amiodarone, cimetidine, ciprofloxacin, delavirdine, fluvoxamine, miconazole, and voriconazole (VFEND). Strong inhibitors of CYP3A4 include atazanavir, clarithromycin, indinavir, itraconazole, ketoconazole, nefazodone, nelfinavir, ritonavir, saquinavir and telithromycin. Moderate inhibitors of CYP3A4 include amprenavir, aprepitant, diltiazem, erythromycin, fluconazole, fosamprenavir, grapefruit juice and verapamil. Additional inhibitors of CYP3A4 include acitretin, cyclosporine, danazol, diethyldithiocarbamate, efavirenz, ethinyl estradiol, fluoxetine, gestodene, imatinib, isoniazid, metronidazole, methylpredisolone, mifepristone, nicardipine, nifedipine, norethindrone, norfloxacin, norfluoxetine, oxiconazole, pomegranate, prednisone, quinine, ranolazine, roxithromycin, sertraline, Synercid, troleandomycin, zafirlukast, and zileuton. Other inhibitors of CYP3A4 include doxycycline, echinacea, and enoxacin.

Inhibitors of CYP2C9 include cimetidine, delavirdine, efavirenz, fenofibrate (Tricor), fluoxetine, fluvastatin, fluvoxamine, isoniazid, ketoconazole, leflunomide, modafinil, sertraline, voriconazole (VFEND), and zafirlukast (Accolate). Moderate inhibitors of CYP2C9 include amiodarone, fluconazole and oxandrolone. Additional CYP2C9 inhibitors include atazanavir, chloramphenicol, clopidogrel, cotrimoxazole, cranberry, disulfiram, fluorouracil, gemfibrozil, ginkgo, imatinib, itraconazole, lovastatin, metronidazole, omeprazole, paroxetine, sulfonamides, triclopidine, and tipranavir. Other inhibitors of CYP2C9 include anastrazole, phenylbutazone, sulfamethoxazole, sulfaphenazole, tamoxifen, teniposide, valproic acid, and 5-fluorouracil.

Inhibitors of CYP2D6 include amiodarone, bupropion, celecoxib, chlorpheniramine, cimetidine, cinacalcet, citalopram, clomipramine, desipramine, diphenhydramine, halofantrine, haloperidol, methadone, moclobemide, propafenone, ritonavir, sertraline, and thioridazine. Strong CYP2D6 inhibitors include fluoxetine, paroxetine and quinidine, while moderate CYP2D6 inhibitors include duloxetine and terbinafine. Additional inhibitors of CYP2D6 include chloroquine, cocaine, darifenacin, escitalopram, fluphenazine, hydroxychloroquine, imatinib, levomepromazine, norfluoxetine, perphenazine, pomegranate, propoxyphene, propranolol, quinacrine, ranitidine, ranolazine, and tipranavir. Other inhibitors of CYP2D6 include amitriptyline, chlorpromazine, doxepin, fluvoxamine, goldenseal, hydroxyzine, imipramine, metoclopramide, pimozide, and ticlopidine (Ticlid).

Inhibitors of CYP2C19 include delavirdine, efavirenz, esomeprazole, felbamate, fluconazole, fluoxetine, fluvoxamine, indomethacin, isoniazid (INH), modafinil (Provigil), oxcarbazepine, ticlopidine, topiramate, and voriconazole (VFEND) A strong inhibitor of CYP2C19 is omeprazole. Additional inhibitors of CYP2C19 include citalopram, fluvastatin, ketoconazole, lansoprazole, letrozole, paroxetine, sertraline, telmisartan, and tipranavir. Other inhibitors of CYP2C19 include artemisinin, chloramphenicol, and oral contraceptives.

Inhibitors of CYP2B6 include clopidogrel (Plavix), efavirenz, fluoxetine, fluvoxamine, ketoconazole, memantine, nelfinavir, oral contraceptives, paroxetine, ritonavir, thiotepa, and ticlopidine (Ticlid).

Avoiding or Discontinuing Administration of a Drug to Avoid Adverse Drug Interactions with Pirfenidone As used herein, "avoiding" means "refraining from." *Merriam-Webster Online Dictionaiy*, 11$^{th}$ ed., 24 Nov. 2009. In some aspects, the invention provides a method of administering pirfenidone therapy to a patient in need of pirfenidone therapy (e.g., a patient with IPF), involving administering to the patient a therapeutically effective amount of pirfenidone, and avoiding administration of a drug that is a moderate-strong inhibitor of both CYP1A2 and another CYP enzyme selected from the group consisting of CYP2C9, CYP2C19 and/or CYP3A4, or a drug that is a moderate to strong inhibitor of both CYP1A2 and another CYP enzyme selected from the group consisting of CYP3A4, CYP2C9, CYP2C19, CYP2B6, and/or CYP2D6. In some embodiments, the drug is fluvoxamine.

In some aspects, the invention provides a method of administering pirfenidone therapy to a patient in need of pirfenidone therapy (e.g., a patient with IPF), involving administering to the patient a therapeutically effective amount of pirfenidone, and avoiding administration of a moderate-strong inhibitor of both CYP1A2 and another CYP enzyme selected from the group consisting of CYP1A1, CYP2A6, CYP2B6, CYP2C8, CYP2C9, CYP2C18, CYP2C19, CYP2D6, CYP2E1, CYP2J2 CYP3A4, CYP3A5, CYP4A11 and/or CYP4F2.

In some aspects, the invention provides a method of administering pirfenidone therapy to a patient in need of pirfenidone therapy (e.g., a patient with IPF), involving administering to the patient a therapeutically effective amount of pirfenidone, and avoiding administration of a strong CYP1A2 inhibitor.

In some aspects, the invention provides a method of administering pirfenidone therapy to a patient in need of pirfenidone therapy (e.g., a patient with IPF), involving administering to the patient a therapeutically effective amount of pirfenidone, and avoiding administration of a CYP1A2 substrate.

In other aspects, the invention provides a method of administering pirfenidone therapy to a patient in need of pirfenidone therapy, comprising discontinuing administration of a drug that is a moderate-strong inhibitor of both CYP1A2 and another CYP enzyme selected from the group consisting of CYP2C9, CYP2C19 and/or CYP3A4 to avoid an adverse drug interaction, and administering a therapeutically effective amount of pirfenidone. In some embodiments, the drug being discontinued is a drug that is a moderate to strong inhibitor of both CYP1A2 and another CYP enzyme selected from the group consisting of CYP3A4, CYP2C9, CYP2C19, CYP2B6, and/or CYP2D6. In some embodiments, the drug is fluvoxamine.

In some aspects, the invention provides a method of administering pirfenidone therapy to a patient in need of pirfenidone therapy, comprising discontinuing administration of a drug that is a moderate-strong inhibitor of both CYP1A2 and another CYP enzyme selected from the group consisting of CYP1A1, CYP2A6, CYP2B6, CYP2C8, CYP2C9, CYP2C18, CYP2C19, CYP2D6, CYP2E1, CYP2J2 CYP3A4, CYP3A5, CYP4A11 and/or CYP4F2 to avoid an adverse drug interaction, and administering a therapeutically effective amount of pirfenidone.

In other aspects, the invention provides a method of administering pirfenidone therapy to a patient in need of pirfenidone therapy, comprising discontinuing administration of a drug that is a strong CYP1A2 inhibitor to avoid an adverse drug interaction, and administering a therapeutically effective amount of pirfenidone.

In one example, in a method of administering a therapeutically effective amount of pirfenidone to a patient with IPF, the invention provides an improvement that comprises avoiding or discontinuing administration of the drug that is a CYP inhibitor and administering a therapeutically effective amount of pirfenidone.

In some embodiments, the drug that is a CYP inhibitor is discontinued concurrent with starting administration of pirfenidone. In other embodiments, the drug that is a CYP inhibitor is discontinued within at least 3 days to 1 month prior to or after starting pirfenidone therapy. This time period, for example, permits adequate time for tapering and withdrawal without adverse effects.

In some embodiments in which fluvoxamine is discontinued to avoid an adverse drug interaction, fluvoxamine is discontinued within at least 3 days prior to or after starting pirfenidone therapy. In various embodiments, fluvoxamine is discontinued within at least 4 days, or at least 5 days, or at least 6 days, or at least 7 days (or one week), or at least 8 days, or at least 9 days, or at east 10 days, or at least 11 days, or at least 12 days, or at least 13 days, or at least 14 days (or two weeks), or at least 15 days, or at least 16 days, or at least 17 days, or at least 18 days, or at least 19 days, or at least 20 days, or at least 21 days (or three weeks), or at least 22 days, or at least 23 days, or at least 24 days, or at least 25 days, or at least 26 days, or at least 27 days, or at least 28 days (or four weeks), or at least 29 days, or at least 30 days, or at least one month, prior to or after starting pirfenidone therapy. In some embodiments, the fluvoxamine is discontinued no earlier than one month, 3 weeks, 2 weeks or 1 week before starting pirfenidone therapy. Preferably, sufficient time is allowed for tapering and/or withdrawal of fluvoxamine therapy.

In some embodiments in which the drug being discontinued is a CYP inhibitor, the drug is discontinued within at least 3 days prior to or after starting pirfenidone therapy. In various embodiments, the drug that is a CYP inhibitor is discontinued within at least 4 days, or at least 5 days, or at least 6 days, or at least 7 days (or one week), or at least 8 days, or at least 9 days, or at least 10 days, or at least 11 days, or at least 12 days, or at least 13 days, or at least 14 days (or two weeks), or at least 15 days, or at least 16 days, or at least 17 days, or at least 18 days, or at least 19 days, or at least 20 days, or at least 21 days (or three weeks), or at least 22 days, or at least 23 days, or at least 24 days, or at least 25 days, or at least 26 days, or at least 27 days, or at least 28 days (or four weeks), or at least 29 days, or at least 30 days, or at least one month, prior to or after starting pirfenidone therapy. In some embodiments, the drug that is a CYP inhibitor is discontinued no earlier than one month, 3 weeks, 2 weeks or 1 week before starting pirfenidone therapy. Preferably, sufficient time is allowed for tapering and/or withdrawal of the drug upon discontinuation.

In some aspects, the invention provides a method of administering pirfenidone therapy to a patient in need of pirfenidone therapy, comprising discontinuing administration of the CYP1A2 substrate to avoid an adverse drug interaction and administering a therapeutically effective amount of pirfenidone. In some embodiments, the drug that is a CYP1A2 substrate is discontinued concurrent with starting administration of pirfenidone. In other embodiments, the drug that is a CYP1A2 substrate is discontinued within at least 3 days to 1 month prior to or after starting pirfenidone therapy. This time period, for example, permits adequate time for tapering and withdrawal without adverse effects.

In some embodiments in which a CYP1A2 substrate is discontinued to avoid an adverse drug interaction, the CYP1A2 substrate is discontinued within at least 3 days prior to or after starting pirfenidone therapy. In various embodiments, the CYP1A2 substrate is discontinued within at least 4 days, or at least 5 days, or at least 6 days, or at least 7 days (or one week), or at least 8 days, or at least 9 days, or at least 10 days, or at least 11 days, or at least 12 days, or at least 13 days, or at least 14 days (or two weeks), or at least 15 days, or at least 16 days, or at least 17 days, or at least 18 days, or at least 19 days, or at least 20 days, or at least 21 days (or three weeks), or at least 22 days, or at least 23 days, or at least 24 days, or at least 25 days, or at least 26 days, or at least 27 days, or at least 28 days (or four weeks), or at least 29 days, or at least 30 days, or at least one month, prior to or after starting pirfenidone therapy. In some embodiments, the CYP1A2 substrate is discontinued no earlier than one month, 3 weeks, 2 weeks or 1 week before starting pirfenidone therapy. Preferably, sufficient time is allowed for tapering and/or withdrawal of the CYP1A2 substrate therapy.

Selecting an Alternative Drug to Administer Concurrently with Pirfenidone Therapy In some aspects, the invention provides a method of administering pirfenidone therapy to a patient in need of pirfenidone therapy and in need of therapy with a drug that is a moderate-strong inhibitor of both CYP1A2 and another CYP enzyme selected from the group consisting of CYP1A1, CYP2A6, CYP2B6, CYP2C8, CYP2C9, CYP2C18, CYP2C19, CYP2D6, CYP2E1, CYP2J2 CYP3A4, CYP3A5, CYP4A11 and/or CYP4F2, comprising administering a therapeutically effective amount of pirfenidone to the patient, and administering an alternative therapy that is not a moderate-strong inhibitor of both CYP1A2 and another CYP enzyme selected from the group consisting of CYP1A1, CYP2A6, CYP2B6, CYP2C8, CYP2C9, CYP2C18, CYP2C19, CYP2D6, CYP2E1, CYP2J2 CYP3A4, CYP3A5, CYP4A11 and/or CYP4F2.

In another embodiment, the invention provides a method of administering pirfenidone therapy to a patient in need of pirfenidone therapy and in need of therapy with a drug that is a moderate-strong inhibitor of both CYP1A2 and another CYP enzyme selected from the group consisting of CYP2C9, CYP2C19, CYP3A4, CYP2B6 and/or CYP2D6, comprising administering a therapeutically effective amount of pirfenidone to the patient, and administering an alternative therapy that is not a moderate-strong inhibitor of both CYP1A2 and another CYP enzyme selected from the group consisting of CYP2C9, CYP2C19, CYP3A4, CYP2B6 and/or CYP2D6.

In some embodiments, the invention provides a method of administering pirfenidone therapy to a patient in need of pirfenidone therapy and in need of therapy with a drug that is a moderate-strong inhibitor of both CYP1A2 and another CYP enzyme selected from the group consisting of CYP2C9, CYP2C19, and/or CYP3A4, comprising administering a therapeutically effective amount of pirfenidone to the patient, and administering an alternative therapy that is not a moderate-strong inhibitor of both CYP1A2 and another CYP enzyme selected from the group consisting of CYP2C9, CYP2C19, and/or CYP3A4.

In other aspects, the invention provides a method of administering pirfenidone therapy to a patient in need of pirfenidone therapy and in need of therapy with a drug that is a strong CYP1A2 inhibitor, comprising administering a therapeutically effective amount of pirfenidone to the patient, and administering an alternative therapy that is not a strong CYP1A2 inhibitor.

In yet other aspects, the invention provides a method of administering pirfenidone therapy to a patient in need of pirfenidone therapy and in need of therapy with a drug that is a CYP1A2 substrate, comprising administering a therapeutically effective amount of pirfenidone to the patient, and administering an alternative therapy that is not a CYP1A2 substrate.

Improving Administration of Pirfenidone by Advising or Cautioning Patient

The administration of a therapeutically effective amount of pirfenidone to a patient in need of pirfenidone therapy can be improved. In some embodiments, the patient is advised that co-administration of pirfenidone with drugs that are a moderate-strong inhibitor of both CYP1A2 and another CYP enzyme selected from the group consisting of CYP2C9, CYP2C19 and/or CYP3A4 can alter the therapeutic effect or adverse reaction profile of pirfenidone. In some embodiments, the patient is advised that co-administration of pirfenidone with fluvoxamine can alter the therapeutic effect or adverse reaction profile of pirfenidone. In some embodiments, the patient is advised that co-administration of pirfenidone with drugs that are a moderate-strong inhibitor of both CYP1A2 and another CYP enzyme selected from the group consisting of CYP1A1, CYP2A6, CYP2B6, CYP2C8, CYP2C9, CYP2C18, CYP2C19, CYP2D6, CYP2E1, CYP2J2 CYP3A4, CYP3A5, CYP4A11 and/or CYP4F2, can alter the therapeutic effect or adverse reaction profile of pirfenidone. In some embodiments, the patient is advised that co-administration of pirfenidone with a drug that is a strong CYP1A2 inhibitor can alter the therapeutic effect or adverse reaction profile of pirfenidone. In some embodiments, the patient is advised that co-administration of pirfenidone with a drug that is a CYP1A2 substrate can alter the therapeutic effect or adverse reaction profile of pirfenidone.

In some embodiments, the patient is advised that use of pirfenidone in patients being treated with fluvoxamine is contraindicated. In some embodiments, the patient is advised that co-administration of pirfenidone and fluvoxamine resulted in a 6-fold increase in exposure to pirfenidone.

In some embodiments, the patient is advised that use of pirfenidone in patients being treated with a drug that is a moderate-strong inhibitor of both CYP1A2 and another CYP enzyme selected from the group consisting of CYP2C9, CYP2C19 and/or CYP3A4 is contraindicated. In some embodiments, the patient is advised that pirfenidone should be used with caution in patients taking a drug that is a moderate-strong inhibitor of both CYP1A2 and another CYP enzyme selected from the group consisting of CYP2C9, CYP2C19 and/or CYP3A4.

In some embodiments, the patient is advised that use of pirfenidone in patients being treated with a drug that is a moderate-strong inhibitor of both CYP1A2 and another CYP enzyme selected from the group consisting of CYP2C9, CYP2C19, CYP3A4, CYP2B6 and/or CYP2D6 is contraindicated. In some embodiments, the patient is advised that pirfenidone should be used with caution in patients taking a drug that is a moderate-strong inhibitor of both CYP1A2 and another CYP enzyme selected from the group consisting of CYP2C9, CYP2C19, CYP3A4, CYP2B6 and/or CYP2D6.

Dosing and Dose Modifications

In various embodiments, a method of administering pirfenidone and fluvoxamine concurrently is provided wherein the patient is administered a therapeutically effective amount of fluvoxamine and a dosage of pirfenidone that is decreased relative to a patient not taking fluvoxamine. In some aspects, such a decreased dosage of pirfenidone is less than 2400 mg/day. For example, the decreased dosage is about 2136 mg per day, 1869 mg per day, 1602 mg per day, 1335 mg per day, or 1068 mg per day (e.g., 8, 7, 6, 5, 4, or 3 capsules per day where each capsule is approximately 267 mg). In some embodiments, the patient is already being administered fluvoxamine. In other embodiments, the patient is already being administered pirfenidone. In related embodiments, the dosage of pirfenidone is decreased prior to administration of fluvoxamine.

In other aspects, a method of administering pirfenidone and a drug that is a moderate-strong inhibitor of both CYP1A2 and another CYP enzyme selected from the group consisting of CYP1A1, CYP2A6, CYP2B6, CYP2C8, CYP2C9, CYP2C18, CYP2C19, CYP2D6, CYP2E1, CYP2J2 CYP3A4, CYP3A5, CYP4A11 and/or CYP4F2 concurrently is provided wherein the patient is administered a therapeutically effective amount of the drug that is a CYP inhibitor and a dosage of pirfenidone that is decreased relative to a patient not taking such drug that is a CYP inhibitor. In some aspects, such a decreased dosage of pirfenidone is less than 2400 mg/day. For example, the decreased dosage is about 2136 mg per day, 1869 mg per day, 1602 mg per day, 1335 mg per day, or 1068 mg per day (e.g., 8, 7, 6, 5, 4, or 3 capsules per day where each capsule is approximately 267 mg). In some embodiments, the patient is already being administered the drug that is a CYP inhibitor. In other embodiments, the patient is already being administered pirfenidone. In related embodiments, the dosage of pirfenidone is decreased prior to administration of the drug that is a CYP inhibitor.

In other aspects, a method of administering pirfenidone and a drug that is a moderate-strong inhibitor of both CYP1A2 and another CYP enzyme selected from the group consisting of CYP2C9, CYP2C19 and/or CYP3A4 concurrently is provided, wherein the patient is administered a therapeutically effective amount of the drug that is a CYP inhibitor and a dosage of pirfenidone that is decreased relative to a patient not taking such drug that is a CYP inhibitor. In related aspects, a method of administering pirfenidone and a drug that is a moderate-strong inhibitor of both CYP1A2 and another CYP enzyme selected from the group consisting of CYP2C9, CYP2C19, CYP3A4, CYP2B6 and/or CYP2D6 concurrently is provided, wherein the patient is administered a therapeutically effective amount of the drug that is a CYP inhibitor and a dosage of pirfenidone that is decreased relative to a patient not taking such drug that is a CYP inhibitor. In some aspects, such a decreased dosage of pirfenidone is less than 2400 mg/day. For example, the decreased dosage is about 2136 mg per day, 1869 mg per day, 1602 mg per day, 1335 mg per day, or 1068 mg per day (e.g., 8, 7, 6, 5, 4, or 3 capsules per day where each capsule is approximately 267 mg). In some embodiments, the patient is already being administered the drug that is a CYP inhibitor. In other embodiments, the patient is already being administered pirfenidone. In related embodiments, the dosage of pirfenidone is decreased prior to administration of the drug that is a CYP inhibitor.

In yet other aspects, a method of administering pirfenidone and a strong CYP1A2 inhibitor concurrently is provided wherein the patient is administered a therapeutically effective amount of the strong CYP1A2 inhibitor and a dosage of pirfenidone that is decreased relative to a patient not taking the strong CYP1A2 inhibitor. In some aspects, such a decreased dosage of pirfenidone is less than 2400 mg/day. For example, the decreased dosage is about 2136 mg per day, 1869 mg per day, 1602 mg per day, 1335 mg per day, or 1068 mg per day (e.g., 8, 7, 6, 5, 4, or 3 capsules per day where each capsule is approximately 267 mg). In some embodiments, the patient is already being administered the strong CYP1A2 inhibitor. In other embodiments, the patient is already being administered pirfenidone. In related embodiments, the dosage of pirfenidone is decreased prior to administration of the strong CYP1A2 inhibitor.

In various embodiments, a method of administering pirfenidone and a CYP1A2 substrate concurrently is provided wherein the patient is administered a therapeutically effective amount of the CYP1A2 substrate and a dosage of pirfenidone that is decreased relative to a patient not taking the CYP1A2 substrate. In some aspects, such a decreased dosage of pirfenidone is less than 2400 mg/day. For example, the decreased dosage is about 2136 mg per day, 1869 mg per day, 1602 mg per day, 1335 mg per day, or 1068 mg per day (e.g., 8, 7, 6, 5, 4, or 3 capsules per day where each capsule is approximately 267 mg). In some embodiments, the patient is already being administered the CYP1A2 substrate. In other embodiments, the patient is already being administered pirfenidone. In related embodiments, the dosage of pirfenidone is decreased prior to administration of the CYP1A2 substrate.

In some embodiments, the amount of pirfenidone being administered is 2400 or 2403 mg/day. Pirfenidone can be dosed at a total amount of about 50 to about 2400 mg per day. The dosage can be divided into two or three doses over the day or given in a single daily dose. Specific amounts of the total daily amount of the therapeutic contemplated for the disclosed methods include about 50 mg, about 100 mg, about 150 mg, about 200 mg, about 250 mg, about 267 mg, about 300 mg, about 350 mg, about 400 mg, about 450 mg, about 500 mg, about 534 mg, about 550 mg, about 600 mg, about 650 mg, about 700 mg, about 750 mg, about 800 mg, about 850 mg, about 900 mg, about 950 mg, about 1000 mg, about 1050 mg, about 1068 mg, about 1100 mg, about 1150 mg, about 1200 mg, about 1250 mg, about 1300 mg, about 1335 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1869 mg, about 1900 mg, about 1950 mg, about 2000 mg, about 2050 mg, about 2100 mg, about 2136 mg, about 2150 mg, about 2200 mg, about 2250 mg, about 2300 mg, about 2350 mg, and about 2400 mg.

Dosages of pirfenidone can alternately be administered as a dose measured in mg/kg. Contemplated mg/kg doses of the disclosed therapeutics include about 1 mg/kg to about 40 mg/kg. Specific ranges of doses in mg/kg include about 1 mg/kg to about 20 mg/kg, about 5 mg/kg to about 20 mg/kg, about 10 mg/kg to about 20 mg/kg, about 10 mg/kg to about 30 mg/kg, and about 15 mg/kg to about 25 mg/kg.

In one embodiment, a dosage amount of pirfenidone is taken with food. In another embodiment, the patient is instructed to administer the dosage of pirfenidone with food.

In some embodiments, a method of administering a SSRI to a patient in need thereof is provided, the improvement comprising discontinuing administration of fluvoxamine, for example, concurrent with starting administration of pirfenidone, and optionally administering an SSRI that is not a moderate to strong inhibitor of both CYP1A2, and a CYP enzyme selected from the group consisting of CYP2C9, CYP2C19 and/or CYP3A4.

In some embodiments, a method of optimizing pirfenidone therapy is provided comprising titrating the dosage of pirfenidone administered to a patient downward relative to a previously administered dosage in the patient, wherein co-administration of fluvoxamine to the patient does not result in an increased exposure to pirfenidone. In some embodiments, the dose is reduced by about 100 mg/day. In other embodiments, the dose is reduced by about 150 mg/day, or about 200 mg/day, or about 250 mg/day, or about 267 mg/day, or about 300 mg/day, or about 350 mg/day, or about 400 mg/day, or about 450 mg/day, or about 500 mg/day, or about 550 mg/day, or about 600 mg/day, or about 650 mg/day, or about 700 mg/day, or about 750 mg/day, or about 800 mg/day, or about 850 mg/day, or about 900 mg/day, or about 950 mg/day, or about 1000 mg/day, or about 1050 mg/day, or about 1100 mg/day, or about 1150 mg/day, or about 1200 mg/day, or about 1250 mg/day, or about 1300 mg/day, or about 1350 mg/day, or about 1400 mg/day, or about 1450 mg/day, or about 1500 mg/day, or about 1600 mg/day or more.

In some embodiments, a method of optimizing pirfenidone therapy is provided comprising titrating the dosage of pirfenidone administered to a patient downward relative to a previously administered dosage in the patient, wherein co-administration of a drug that is a moderate-strong inhibitor of both CYP1A2 and another CYP enzyme selected from the group consisting of CYP1A1, CYP2A6, CYP2B6, CYP2C8, CYP2C9, CYP2C18, CYP2C19, CYP2D6, CYP2E1, CYP2J2 CYP3A4, CYP3A5, CYP4A11 and/or CYP4F2 to the patient does not result in an increased exposure to pirfenidone. In some embodiments, the dose is reduced by about 100 mg/day. In other embodiments, the dose is reduced by about 150 mg/day, or about 200 mg/day, or about 250 mg/day, or about 267 mg/day, or about 300 mg/day, or about 350 mg/day, or about 400 mg/day, or about 450 mg/day, or about 500 mg/day, or about 550 mg/day, or about 600 mg/day, or about 650 mg/day, or about 700 mg/day, or about 750 mg/day, or about 800 mg/day, or about 850 mg/day, or about 900 mg/day, or about 950 mg/day, or about 1000 mg/day, or about 1050 mg/day, or about 1100 mg/day, or about 1150 mg/day, or about 1200 mg/day, or about 1250 mg/day, or about 1300 mg/day, or about 1350 mg/day, or about 1400 mg/day, or about 1450 mg/day, or about 1500 mg/day, or about 1600 mg/day or more.

In some embodiments, a method of optimizing pirfenidone therapy is provided comprising titrating the dosage of pirfenidone administered to a patient downward relative to a previously administered dosage in the patient, wherein co-administration of a drug that is a moderate-strong inhibitor of both CYP1A2 and another CYP enzyme selected from the group consisting of CYP2C9, CYP2C19 and/or CYP3A4 to the patient does not result in an increased exposure to pirfenidone. In some embodiments, a method of optimizing pirfenidone therapy is provided comprising titrating the dosage of pirfenidone administered to a patient downward relative to a previously administered dosage in the patient, wherein co-administration of a drug that is a moderate-strong inhibitor of both CYP1A2 and another CYP enzyme selected from the group consisting of CYP2C9, CYP2C19, CYP3A4, CYP2B6 and/or CYP2D6 to the patient does not result in an increased exposure to pirfenidone. In some embodiments, the dose is reduced by about 100 mg/day. In other embodiments, the dose is reduced by about 150 mg/day, or about 200 mg/day, or about 250 mg/day, or about 267 mg/day, or about 300 mg/day, or about 350 mg/day, or about 400 mg/day, or about 450 mg/day, or about 500 mg/day, or about 550 mg/day, or about 600 mg/day, or about 650 mg/day, or about 700 mg/day, or about 750 mg/day, or about 800 mg/day, or about 850 mg/day, or about 900 mg/day, or about 950 mg/day, or about 1000 mg/day, or about 1050 mg/day, or about 1100 mg/day, or about 1150 mg/day, or about 1200 mg/day, or about 1250 mg/day, or about 1300 mg/day, or about 1350 mg/day, or about 1400 mg/day, or about 1450 mg/day, or about 1500 mg/day, or about 1600 mg/day or more.

In some embodiments, a method of optimizing pirfenidone therapy is provided comprising titrating the dosage of pirfenidone administered to a patient downward relative to a previously administered dosage in the patient, wherein co-administration of a strong CYP1A2 inhibitor to the patient does not result in an increased exposure to pirfenidone. In some embodiments, the dose is reduced by about 100 mg/day. In other embodiments, the dose is reduced by about 150 mg/day, or about 200 mg/day, or about 250 mg/day, or about 267 mg/day, or about 300 mg/day, or about 350 mg/day, or about 400 mg/day, or about 450 mg/day, or about 500 mg/day, or about 550 mg/day, or about 600 mg/day, or about 650 mg/day, or about 700 mg/day, or about 750 mg/day, or about 800 mg/day, or about 850 mg/day, or about 900 mg/day, or about 950 mg/day, or about 1000 mg/day, or about 1050 mg/day, or about 1100 mg/day, or about 1150 mg/day, or about 1200 mg/day, or about 1250 mg/day, or about 1300 mg/day, or about 1350 mg/day, or about 1400 mg/day, or about 1450 mg/day, or about 1500 mg/day, or about 1600 mg/day or more.

In some embodiments, a method of optimizing pirfenidone therapy is provided comprising titrating the dosage of pirfenidone administered to a patient downward relative to a previously administered dosage in the patient, wherein co-administration of a CYP1A2 substrate to the patient does not result in an increased exposure to pirfenidone. In some embodiments, the dose is reduced by about 100 mg/day. In other embodiments, the dose is reduced by about 150 mg/day, or about 200 mg/day, or about 250 mg/day, or about 267 mg/day, or about 300 mg/day, or about 350 mg/day, or about 400 mg/day, or about 450 mg/day, or about 500 mg/day, or about 550 mg/day, or about 600 mg/day, or about 650 mg/day, or about 700 mg/day, or about 750 mg/day, or about 800 mg/day, or about 850 mg/day, or about 900 mg/day, or about 950 mg/day, or about 1000 mg/day, or about 1050 mg/day, or about 1100 mg/day, or about 1150 mg/day, or about 1200 mg/day, or about 1250 mg/day, or about 1300 mg/day, or about 1350 mg/day, or about 1400 mg/day, or about 1450 mg/day, or about 1500 mg/day, or about 1600 mg/day or more.

In some embodiments, a method of administering pirfenidone therapy to a patient receiving fluvoxamine therapy is provided, comprising administering to the patient a therapeutically effective amount of fluvoxamine and administering to the patient a daily dosage of pirfenidone that is less than 2400 mg or 2403 mg per day, e.g. 1600 mg or 1602 mg per day. In some embodiments, the dosage of pirfenidone is decreased prior to administration of fluvoxamine. Similarly, in any of the foregoing embodiments relating to other CYP inhibitors or CYP substrates, the daily dosage of pirfenidone that is less than 2400 mg or 2403 mg per day may be, e.g. 1600 mg or 1602 mg per day.

In some embodiments, a method of optimizing pirfenidone therapy is provided comprising titrating the dosage of pirfenidone administered to a patient downward relative to a previously administered dosage in the patient, wherein co-administration of fluvoxamine to the patient does not result in an increased exposure to pirfenidone.

Packages, Kits, Methods of Packaging, and Methods of Delivering

In another aspect, a package or kit is provided comprising pirfenidone, optionally in a container, and a package insert, package label, instructions or other labeling including any one, two, three or more of the following information or recommendations:

(a) use of fluvoxamine should be avoided or discontinued, (b) co-administration of pirfenidone with drugs that are moderate to strong inhibitors of both CYP1A2 and another CYP enzyme selected from the group consisting of CYP3A4, CYP2C9, and/or CYP2C19, can alter the therapeutic effect or adverse reaction profile of pirfenidone, (c) co-administration of pirfenidone with fluvoxamine can alter the therapeutic effect or adverse reaction profile of pirfenidone, (d) use of pirfenidone in patients being treated with fluvoxamine is contraindicated, (e) co-administration of pirfenidone and fluvoxamine resulted in an average 6-fold increase in exposure to pirfenidone, and/or (f) strong CYP1A2 inhibitors should be used with caution in patients receiving pirfenidone due to the potential for reduced pirfenidone clearance.

In some embodiments, the information or recommendation may include that co-administration of pirfenidone and fluvoxamine resulted in a 2-fold increase in average peak serum concentration of pirfenidone (Cmax).

In other embodiments, the information or recommendation may include that co-administration of pirfenidone with drugs that are moderate to strong inhibitors of both CYP1A2 and another CYP enzyme selected from the group consisting of CYP3A4, CYP2C9, CYP2C19, CYP2B6, and/or CYP2D6 can alter the therapeutic effect or adverse reaction profile of pirfenidone. In other embodiments, the information or recommendation may include that co-administration of pirfenidone with drugs that are moderate to strong inhibitors of both CYP1A2 and another CYP enzyme selected from the group consisting of CYP1A1, CYP2A6, CYP2B6, CYP2C8, CYP2C9, CYP2C18, CYP2C19, CYP2D6, CYP2E1, CYP2J2 CYP3A4, CYP3A5, CYP4A11 and/or CYP4F2 can alter the therapeutic effect or adverse reaction profile of pirfenidone. In other embodiments, the information or recommendation may include that co-administration of pirfenidone with drugs that are strong CYP1A2 inhibitors can alter the therapeutic effect or adverse reaction profile of pirfenidone. In other embodiments, the information or recommendation may include that co-administration of pirfenidone with drugs that are CYP1A2 substrates can alter the therapeutic effect or adverse reaction profile of pirfenidone.

In other embodiments, the information or recommendation may include that drugs that are moderate to strong inhibitors of both CYP1A2 and another CYP enzyme selected from the group consisting of CYP3A4, CYP2C9, and/or CYP2C19 should be avoided or discontinued, or are contraindicated, or should be used with caution. In yet further embodiments, the information or recommendation may include that administering a strong CYP1A2 inhibitor should be avoided or discontinued, or are contraindicated, or should be used with caution. In other embodiments, the information or recommendation may include that drugs that are CYP1A2 substrates should be avoided or discontinued, or are contraindicated, or should be used with caution.

The package insert, package label, instructions or other labeling may further comprise directions for treating IPF by administering pirfenidone, e.g., at a dosage of 2400 mg or 2403 mg per day.

In related aspect, the invention provides a method of preparing or packaging a pirfenidone medicament comprising packaging pirfenidone, optionally in a container, together with a package insert or package label or instructions including any one, two, three or more of the foregoing information or recommendations.

In some embodiments, a method of treating IPF is disclosed comprising providing, selling or delivering any of the kits of disclosed herein to a hospital, physician or patient.

In some embodiments, a kit is provided comprising fluvoxamine and a package insert, package label, instructions, or other labeling comprising any one, two, three or more of the following warnings:

(a) use of fluvoxamine and pirfenidone is contraindicated (b) use of pirfenidone in patients being treated with fluvoxamine is contraindicated, and/or (c) co-administration of pirfenidone and fluvoxamine resulted in an average 6-fold increase in exposure to pirfenidone.

(d) co-administration of pirfenidone and fluvoxamine resulted in an average 2-fold increase in peak serum concentration of pirfenidone.

In some embodiments, a method of treating a patient in need of fluvoxamine is provided comprising providing or delivering any of the kits disclosed herein comprising fluvoxamine to a hospital, physician or patient.

In related aspects, the invention provides a method of administering a SSRI to a patient in need thereof, the improvement comprising discontinuing administration of fluvoxamine, for example, concurrent with starting administration of pirfenidone, and optionally administering an SSRI that is not a moderate to strong inhibitor of both CYP1A2 and another CYP enzyme selected from the group consisting of CYP3A4, CYP2C9, and/or CYP2C19.

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

Example 1

An open-label Phase 1 study was performed to determine the impacts of fluvoxamine on the pharmacokinetics and safety of pirfenidone in healthy subjects.

Study Design. The study was a Phase 1, open-label, parallel-group study in healthy subjects. Fifty-four subjects were to be enrolled in two groups, consisting of 27 subjects who were smokers (Group 1) and 27 subjects who were nonsmokers (Group 2). Smoking induces CYP1A2 activity. Each group (smokers and nonsmokers) was to include a minimum of nine females and nine males, and attempts were to be made to enroll equal numbers of each sex in each group. Each subject was to receive a single 801-mg dose of pirfenidone on Days 1 and 11. Fluvoxamine dosing was started on Day 2 and titrated to final dose according to the following schedule:

Days 2-4: fluvoxamine 50 mg at bedtime

Days 5-7: fluvoxamine 50 mg twice a day (in the morning and at bedtime)

Days 8-11: fluvoxamine 50 mg in the morning and 100 mg at bedtime

All pharmacokinetic (PK) analyses were conducted using population PK methods using Monte-Carlo parametric expectation maximization as implemented in the open-source software program S ADAPT 1.5.6 (Bauer et al., *AAPS Journal* 9(1):E60-83, 2007). The structural model for the analysis was obtained from a preliminary population PK analysis. This population PK model was fit to the pirfenidone and 5 carboxy-pirfenidone plasma concentration-time data from Days 1 and 11 separately. Once a final population PK model was defined, $AUC_{0-\infty}$ estimates were generated by simulating plasma PK profiles and compared for statistically significant differences between days (to test the effect of fluvoxamine co-administration) and between groups (to test the effect of smoking status).

As the primary endpoint of the study, differences in the pirfenidone and 5 carboxy pirfenidone $AUC_{0-\infty}$ estimates between Days 1 and 11, and between smokers and nonsmokers were tested for significance. The analysis of the effect of fluvoxamine (i.e., Day 1 versus Day 11) was analyzed using the FDA criteria for bioequivalence for paired data (FDA 2003). The ratio of $AUC_{0-\infty}$ on Day 11 to that on Day 1 was used to test for the interaction between smoking status and fluvoxamine coadministration. If other subject characteristics (such as body size or age) were also associated with the ratio of $AUC_{0-\infty}$ on Day 11 to that on Day 1, the significance of these covariates was also tested. The significance of differences in pirfenidone and 5-carboxy-pirfenidone $AUC_{0-\infty}$ estimates on Day 1 in smokers and nonsmokers was tested using multivariable linear regression in order to take into account the effects of other significant covariates.

Pharmacokinetic Results. Fifty-one of the 54 subjects enrolled in the study were included in the PK analyses. Three subjects were removed from the PK analyses as they did not meet the protocol-specified requirement for adequate compliance with the fluvoxamine dosing regimen. Two subjects discontinued the study early due to adverse events, and one subject only took 73% of the protocol-required fluvoxamine dose. All 51 subjects had the full complement of PK samples available for analysis. Each subject had two profiles on each day: one for pirfenidone and one for 5-carboxy pirfenidone. There were a total of 1224 samples (12 per subject per day); each sample was assayed for pirfenidone and 5-carboxy-pirfenidone for a total of 2448 concentrations.

A robust fit to the data was obtained using the population PK structural model. In general, the fits of the data were excellent: 98% of the individual profiles had $r^2$ values above 0.9 and there was no systematic bias in the fits.

The summary statistics of $AUC_{0-\infty}$ stratified by study day are provided in Table 1. Symmetrical dot density plots of pirfenidone and 5-carboxy pirfenidone $AUC_{0-\infty}$ values versus study day, identified by smoking status, are provided in FIG. 1. The co-administration of fluvoxamine resulted in a significant increase in the $AUC_{0-\infty}$ of pirfenidone (p<0.00001). There was not a statistically significant effect of fluvoxamine co-administration on 5-carboxy pirfenidone $AUC_{0-\infty}$.

TABLE 1

Comparison of $AUC_{0-\infty}$ Between Study Days (n = 51)

| | | $AUC_{0-\infty}$ (mg · hr/L) | |
|---|---|---|---|
| Study Day | Statistic | Pirfenidone[a] | 5-Carboxy-Pirfenidone[b] |
| 1: Pre-Fluvoxamine | Mean (SD) | 34.9 (16.9) | 29.3 (8.22) |
| | Median (25th-75th) | 34.7 (21.4-45.9) | 26.9 (22.0-33.7) |
| 11: Post-Fluvoxamine | Mean (SD) | 171 (47.7) | 31.7 (8.96) |
| | Median (25th-75th) | 167 (126-206) | 29.4 (25.4-36.5) |

[a]p-value < 0.00001 (paired t-test)
[b]p-value = 0.168 (paired t-test)
$AUC_{0-\infty}$ = area under the concentration-time curve from time zero to infinity; SD = standard deviation.

There was also a large apparent difference in the $C_{max}$ estimates pre- and post-fluvoxamine; the pirfenidone $C_{max}$ was higher after administration of fluvoxamine while the 5-carboxy pirfenidone $C_{max}$ was lower after administration of fluvoxamine. The mean (95% CI) for the ratio of $C_{max}$ on Day 11 to the $C_{max}$ on Day 1 was 2.09 (1.94-2.25) for pirfenidone and 0.369 (0.349-0.390) for 5-carboxy-pirfenidone.

The summary statistics of the ratio of the $AUC_{0-\infty}$ on Day 11 to the $AUC_{0-\infty}$ on Day 1, stratified by smoking status, are provided in Table 2. While both smokers and nonsmokers were affected by the coadministration of fluvoxamine, smokers appeared to have a more pronounced increase in exposure to pirfenidone, as evidenced by the higher ratio of Day 11 to Day 1 AUC. Given that there was an imbalance in the demographics between smokers and nonsmokers (smokers were younger, heavier and predominantly male), the impact of these variables on the ratio of the pirfenidone $AUC_{0-\infty}$ on Day 11 to the $AUC_{0-\infty}$ on Day 1 was tested using multiple linear regression. Using backward elimination (p-value for removal=0.10), smoking status was the only significant predictor of the ratio of the pirfenidone $AUC_{0-\infty}$ on Day 11 to the $AUC_{0-\infty}$ on Day 1; body size, sex, and age were not significant.

TABLE 2

Comparison of Ratio of Day 11 $AUC_{0-\infty}$ to Day 1 $AUC_{0-\infty}$ by Smoking Status

| Smoking Status | Statistic | Pirfenidone | 5-Carboxy-Pirfenidone |
|---|---|---|---|
| Smokers | N | 26 | 26 |
| | Mean (SD) | 7.32 (2.12) | 1.12 (0.0951) |
| | Median (25th-75th) | 7.07 (6.12-8.25) | 1.13 (1.04-1.19) |
| Nonsmokers | N | 25 | 25 |
| | Mean (SD) | 4.13 (1.15) | 1.05 (0.114) |
| | Median (25th-75th) | 3.99 (3.26-4.68) | 1.03 (0.978-1.11) |

$AUC_{0-\infty}$ = area under the concentration-time curve from time zero to infinity; SD = standard deviation.

In summary, the design and execution of this study allowed for a robust and informative analysis of the effects of CYP1A2 inhibition on the pharmacokinetics of pirfenidone. Administration of the potent CYP inhibitor fluvoxamine resulted in a significant drug interaction and markedly increased pirfenidone exposure. Smokers were likely to experience significantly lower pirfenidone exposure (in the absence of the drug interaction) presumably due to the inductive effects of smoking.

The coadministration of fluvoxamine resulted in a significant drug interaction such that exposure ($AUC_{0-\infty}$) to pirfenidone was, on average, nearly 6 times higher after ten days of dosing with fluvoxamine. Subjects also experienced, on average, a two-fold increase in $C_{max}$ after administration of fluvoxamine.

While the present invention has been described in terms of various embodiments and examples, it is understood that variations and improvements will occur to those skilled in the art. Therefore, only such limitations as appear in the claims should be placed on the invention.

What is claimed is:

1. A method of administering pirfenidone and fluvoxamine concurrently to a patient in need thereof comprising administering a therapeutically effective amount of fluvoxamine to the patient and administering a therapeutically effective amount of pirfenidone to the patient, wherein the amount of the pirfenidone is about 801 mg/day.

2. The method of claim 1 wherein the pirfenidone is administered three times per day.

3. The method of claim 2 wherein the patient has idiopathic pulmonary fibrosis (IPF).

4. The method of claim 3 wherein the pirfenidone is administered to the patient with food.

5. The method of claim 1 further comprising discontinuing co-administration of fluvoxamine and administering a therapeutically effective amount of pirfenidone.

6. A method of providing pirfenidone therapy to a patient in need thereof comprising titrating the dosage of pirfenidone administered to the patient downward from a dose of about 2400 mg/day, while co-administering fluvoxamine, wherein the dose of pirfenidone is reduced by about 1600 mg/day.

7. The method of claim 6 wherein about 800 mg/day of pirfenidone is administered to the patient.

8. The method of claim 6 wherein the pirfenidone is administered three times per day.

9. The method of claim 8 wherein the patient has idiopathic pulmonary fibrosis (IPF).

10. The method of claim 9 wherein the pirfenidone is administered to the patient with food.

11. The method of claim 6 further comprising discontinuing co-administration of fluvoxamine and administering about 2400 mg/day of pirfenidone.

\* \* \* \* \*